US009245675B2

(12) United States Patent
Tsai et al.

(10) Patent No.: US 9,245,675 B2
(45) Date of Patent: Jan. 26, 2016

(54) GENERATING APPARATUS OF A PULSED MAGNETIC FIELD

(71) Applicant: NATIONAL SYNCHROTRON RADIATION RESEARCH CENTER, Hsinchu (TW)

(72) Inventors: Kuang Lung Tsai, Hsinchu (TW); Chyi Shyan Fann, Hsinchu (TW); San Yuang Hsu, Hsinchu (TW); Ke Kang Lin, Hsinchu (TW)

(73) Assignee: NATIONAL SYNCHROTRON RADIATION RESEARCH CENTER, Hsinchu (TW)

( * ) Notice: Subject to any disclaimer, the term of this patent is extended or adjusted under 35 U.S.C. 154(b) by 195 days.

(21) Appl. No.: 14/083,073

(22) Filed: Nov. 18, 2013

(65) Prior Publication Data

US 2015/0141736 A1    May 21, 2015

(51) Int. Cl.
H01F 5/00 (2006.01)
H01F 3/00 (2006.01)
A61N 2/00 (2006.01)
A61N 2/02 (2006.01)

(52) U.S. Cl.
CPC ........ H01F 5/00 (2013.01); A61N 2/004 (2013.01); A61N 2/02 (2013.01); H01F 3/00 (2013.01)

(58) Field of Classification Search
CPC ............... H01F 5/00; H01F 3/00; A61N 2/02; A61N 2/004
See application file for complete search history.

(56) References Cited

U.S. PATENT DOCUMENTS

| | | | |
|---|---|---|---|
| 1,844,626 A * | 2/1932 | Anderson | 336/90 |
| 3,895,869 A * | 7/1975 | Lewis | 335/296 |
| 3,932,827 A * | 1/1976 | Buhrer | 336/60 |
| 5,136,273 A | 8/1992 | Ohta | |
| 6,459,348 B1 * | 10/2002 | Birkelund | 335/270 |
| 2003/0076202 A1 * | 4/2003 | Haugs et al. | 335/1 |

FOREIGN PATENT DOCUMENTS

| | | |
|---|---|---|
| CN | 203225147 | 10/2013 |
| JP | 6-120065 | 4/1994 |
| JP | 2004-47849 | 2/2004 |
| JP | 2010-56175 | 3/2010 |

OTHER PUBLICATIONS

Office Action issued Nov. 10, 2015 in corresponding Chinese patent application and partial English translation therof, 7 pages total.

* cited by examiner

*Primary Examiner* — Mohamad Musleh
(74) *Attorney, Agent, or Firm* — Hamre, Schumann, Mueller & Larson, P.C.

(57) ABSTRACT

An apparatus for generating a pulsed magnetic field includes an insulating body, an electrical conductor positioned on the insulating body, and a ferromagnetic body having a hollow portion, wherein the insulating body and the electrical conductor are positioned in the hollow portion. In some embodiments of the present disclosure, the electrical conductor has at least one gap separating the electrical conductor into at least two parts, thereby allowing a current to flow through the at least two parts in parallel to generate a magnetic field in the insulating body.

12 Claims, 8 Drawing Sheets

GENERATING APPARATUS OF A PULSED MAGNETIC FIELD

TECHNICAL FIELD

The present disclosure relates to an apparatus for generating a pulsed magnetic field.

DISCUSSION OF THE BACKGROUND

Low-energy magnetic fields are increasingly used for therapeutic purposes, such as the healing of fractures and ulcers. For example, pulsed electromagnetic fields (PEMF) have been widely used in treating therapeutically resistant problems of the musculoskeletal system. In addition, PEMF is also used for sterilization of foods such as milk, fruits and vegetables. Furthermore, the application of PEMF is to metallurgy has recently been developing.

In particular, PEMF therapy has been used to treat non-union bone fractures and delayed union bone fractures. Non-union bone fractures are typically defined as injuries which have not satisfactorily healed within nine months or more after the fracture occurs. Delayed union fractures are typically considered injuries which have not satisfactorily healed within nine months or less after the fracture occurs. PEMF therapy has also been used for the treatment of corresponding types of body soft tissue injuries.

This "Discussion of the Background" section is provided for background information only. The statements in this "Discussion of the Background" are not an admission that the subject matter disclosed in this "Discussion of the Background" section constitutes prior art to the present disclosure, and no part of this "Discussion of the Background" section may be used as an admission that any part of this application, including this "Discussion of the Background" section, constitutes prior art to the present disclosure.

SUMMARY

One aspect of the present disclosure provides an apparatus for generating a pulsed magnetic field.

An apparatus for generating a pulsed magnetic field according to this aspect of the present disclosure comprises an insulating body, an is electrical conductor positioned on the insulating body, and a ferromagnetic body having a hollow portion, wherein the insulating body and the electrical conductor are positioned in the hollow portion. In some embodiments of the present disclosure, the electrical conductor has at least one gap separating the electrical conductor into at least two parts, thereby allowing a current to flow through the at least two parts in parallel to generate a magnetic field in the insulating body.

The embodiment of the present disclosure introduces the gap in the electrical conductor, and the width ($\Delta x$) of a utilizable field region can be increased without increasing the distance between the first segment and the second segment, i.e., without increasing the size of the entire apparatus.

The foregoing has outlined rather broadly the features and technical advantages of the present disclosure in order that the detailed description of the disclosure that follows may be better understood. Additional features and advantages of the disclosure will be described hereinafter, which form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims.

BRIEF DESCRIPTION OF THE DRAWINGS

A more complete understanding of the present disclosure may be derived by referring to the detailed description and claims when considered in connection with the Figures, where like reference numbers refer to similar elements throughout the Figures, and:

DETAILED DESCRIPTION

The following description of the disclosure accompanies drawings, which are incorporated in and constitute a part of this specification, and illustrate embodiments of the disclosure, but the disclosure is not limited to the embodiments. In addition, the following embodiments can be properly integrated to complete another embodiment.

References to "one embodiment," "an embodiment," "exemplary embodiment," "other embodiments," "another embodiment," etc. indicate that the embodiment(s) of the disclosure so described may include a particular feature, structure, or characteristic, but not every embodiment necessarily includes the particular feature, structure, or characteristic. Further, repeated use of the phrase "in the embodiment" does not necessarily refer to the same embodiment, is although it may.

The present disclosure is directed to an apparatus for generating a pulsed magnetic field. In order to make the present disclosure completely comprehensible, detailed steps and structures are provided in the following description. Obviously, implementation of the present disclosure does not limit special details known by persons skilled in the art. In addition, known structures and steps are not described in detail, so as not to limit the present disclosure unnecessarily. Preferred embodiments of the present disclosure will be described below in detail. However, in addition to the detailed description, the present disclosure may also be widely implemented in other embodiments. The scope of the present disclosure is not limited to the detailed description, and is defined by the claims.

Figure 1:
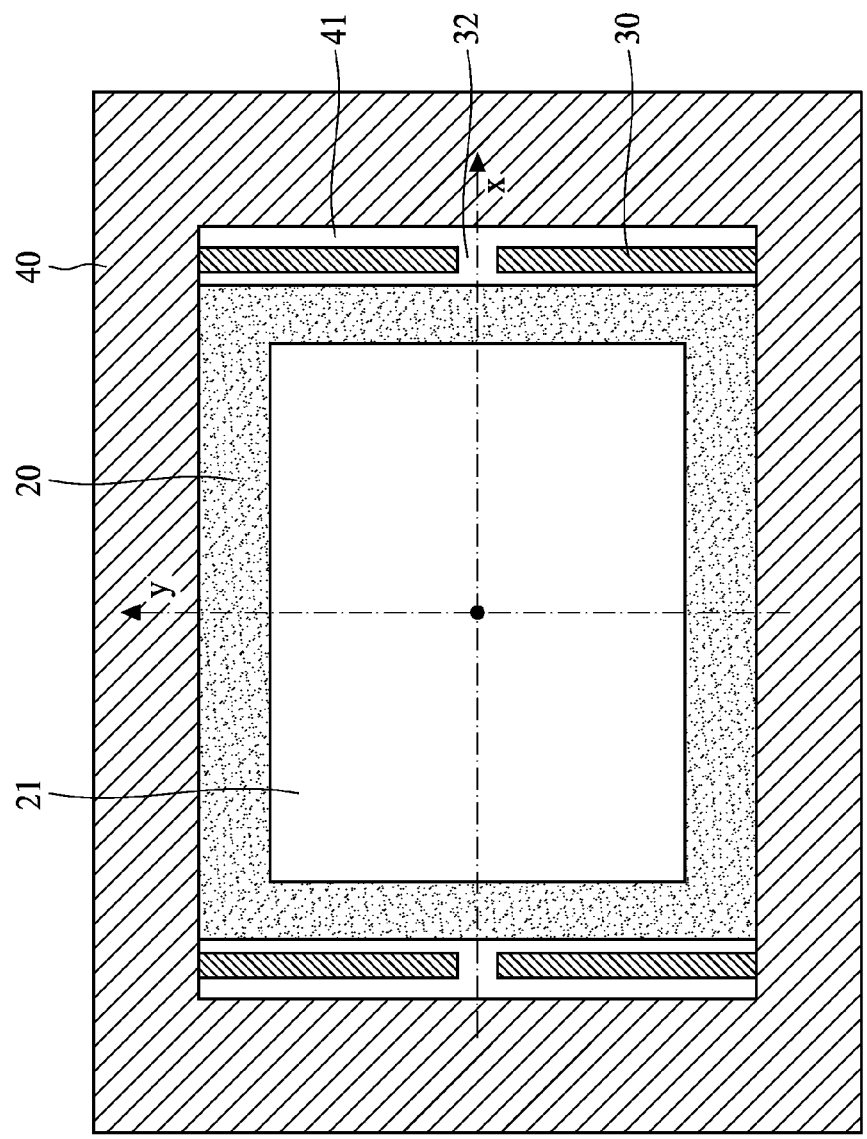
FIG. 1 is a cross-sectional view showing an apparatus 10 for generating a pulsed magnetic field in accordance with embodiments of the inventive arrangements disclosed herein.

FIG. 1 is a cross-sectional view showing an apparatus 10 for generating a pulsed magnetic field in accordance with embodiments of the inventive arrangements disclosed herein. In some embodiments of the present disclosure, the apparatus 10 for a generating pulsed magnetic field comprises an insulating body 20 defining a chamber 21, an electrical conductor 30 positioned on the insulating body 20, and a ferromagnetic body 40 having a hollow portion 41, wherein the insulating body 20 and the electrical conductor 30 are positioned in the hollow portion 41. In some embodiments of the present disclosure, the insulating body 20 is a tube comprising ceramic material, the electrical conductor 30 is encapsulated by an insulating resin, and the ferromagnetic body 40 includes ferrite or silicon steel.

Figure 2:
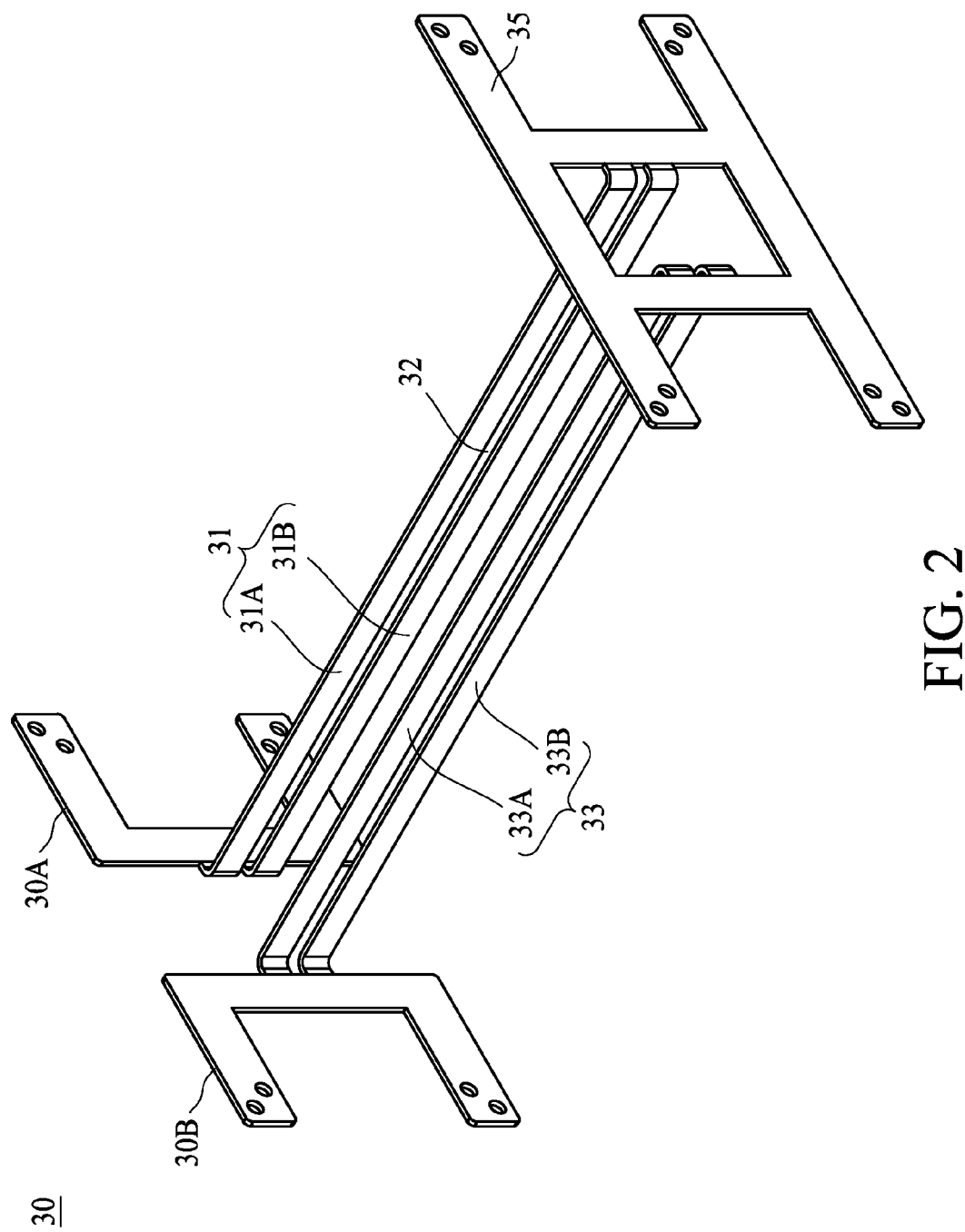
FIG. 2 is a full view of the electrical conductor shown in FIG. 1 in accordance with embodiments of the inventive arrangements disclosed herein.

FIG. 2 is a full view of the electrical conductor 30 shown in FIG. 1 in accordance with embodiments of the inventive arrangements disclosed herein. In some embodiments of the present disclosure, the electrical conductor 30 comprises a first segment 31 positioned on one inner sidewall of the insulating body 20, and a second segment 33 positioned on an opposite inner sidewall of the insulating body 20, i.e., the first segment 31 and the second segment 33 are on opposite sides of the chamber 21. In some embodiments of the present disclosure, the electrical conductor 30 further comprises a third segment 35 connecting the first segment 21 and the second segment 33 for conducting the current in series from an input terminal 30A to an output terminal 30B.

In some embodiments of the present disclosure, the electrical conductor 30 has at least one gap 32 separating the first segment 31 of the electrical conductor 30 into at least two parts such that the current flows through the two parts in parallel to generate a magnetic field in the chamber 21 of the insulating body 20. For example, the first segment 31 is a plate, and the at least one gap 32 separates the first segment 31 into a first upper part 31A and a first lower part 31B; the second segment 33 is a plate, and the at least one gap 32 separates the second segment 33 into a second upper part 33A and a second lower part 33B.

In some embodiments of the present disclosure, the third segment 35 connects the first upper part 31A to the second lower part 33B; in addition, the third segment 35 further connects the first lower part 31B to the second upper part 33A. As a result, the electrical conductor 30 can conduct the current more uniformly so as to generate the magnetic field in the chamber 21 of the insulating body 20 in a more uniform manner.

In some embodiments of the present disclosure, the input terminal 30A connects the first upper part 31A and the first lower part 31B, and the output terminal 30B connects the second upper part 33A and the second lower part 33B. Consequently, the electrical conductor 30 forms a one-turn coil on the insulating body 20 without circumferentially surrounding the insulating body 20.

Figure 3:
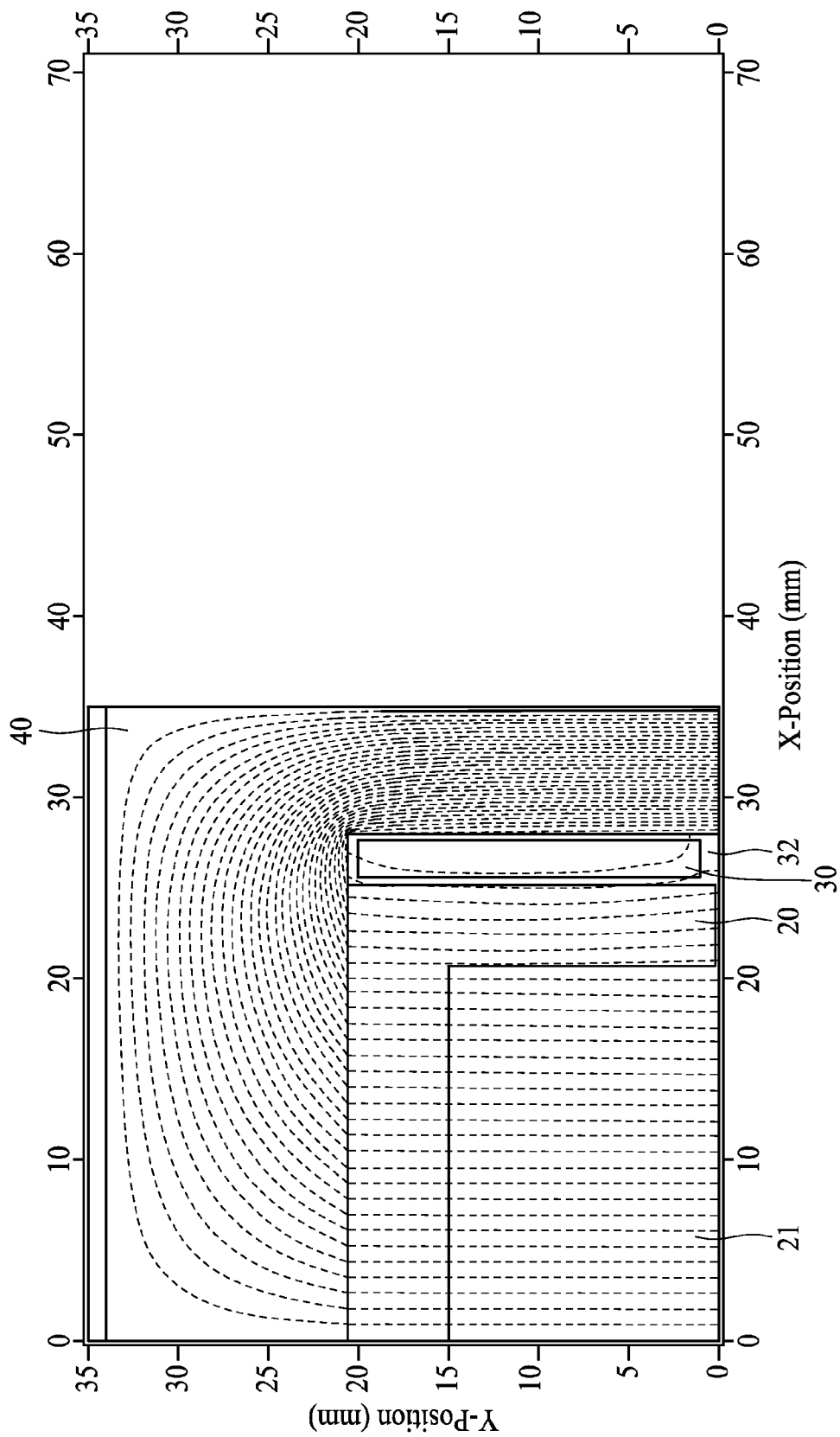
FIG. 3 is a plot showing the distribution of the magnetic field generated by the apparatus in accordance with embodiments of the inventive arrangements disclosed herein.
Figure 4:
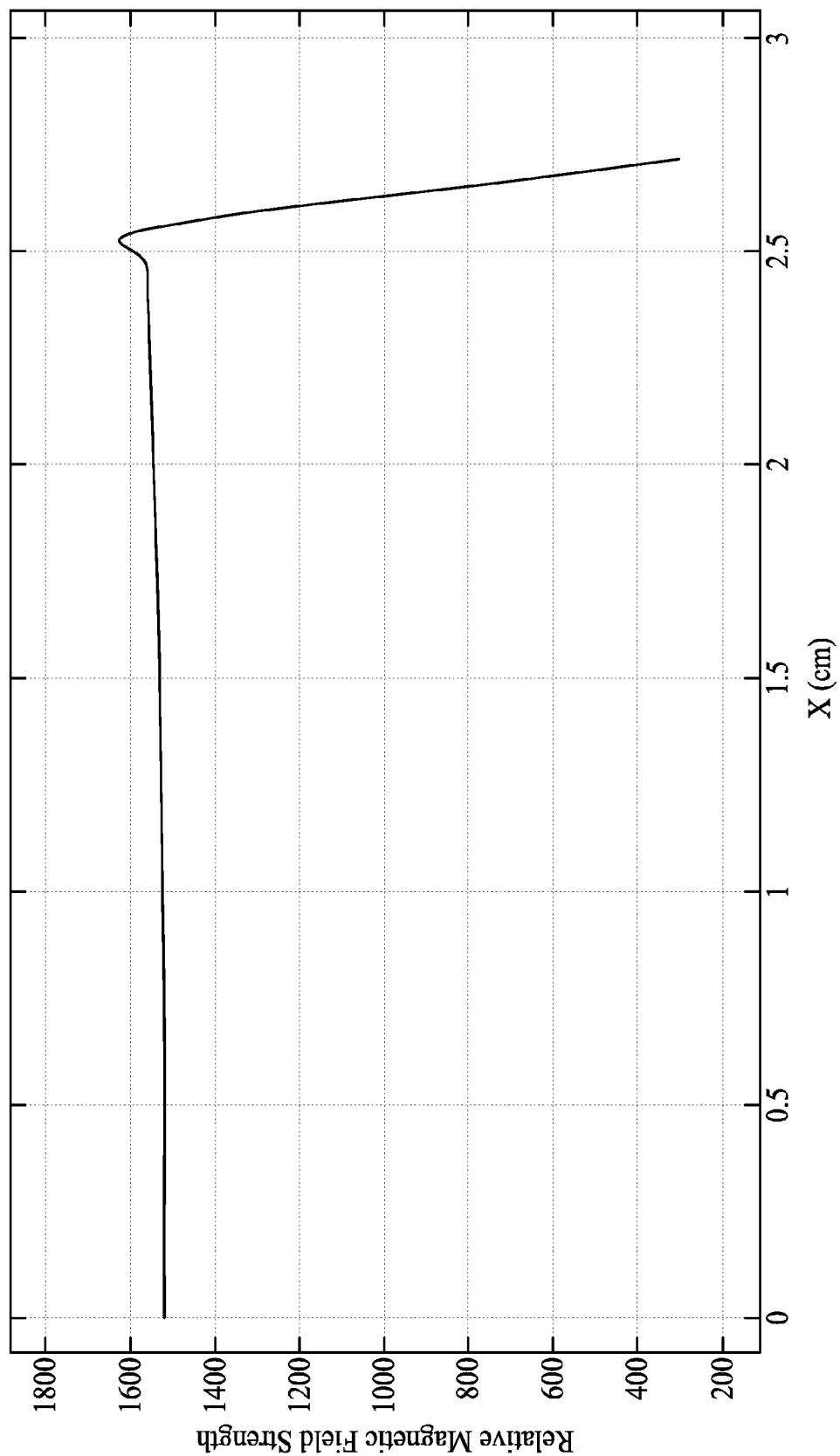
FIG. 4 is a plot showing a relative strength of the magnetic field generated by the apparatus along the X-axis in accordance with embodiments of the inventive arrangements disclosed herein.

FIG. 3 is a plot showing the distribution of the magnetic field generated by the apparatus 10 in accordance with embodiments of the inventive arrangements disclosed herein, and FIG. 4 is a plot showing a relative strength of the magnetic field generated by the apparatus 10 along the X-axis in accordance with embodiments of the inventive arrangements disclosed herein. In the exemplary embodiments used in FIGS. 3-4, the width between the first segment 31 and the second segment 33 is 51.2 cm. In some embodiments of the present disclosure, the apparatus 10 for generating a pulsed magnetic field is designed to be symmetric with respect to both the X-axis and the Y-axis, and FIGS. 3-4 show an upper and right quarter of the apparatus 10, wherein the coordinate (0,0) corresponds to the center of the apparatus 10 for generating the pulsed magnetic field.

Figure 5:
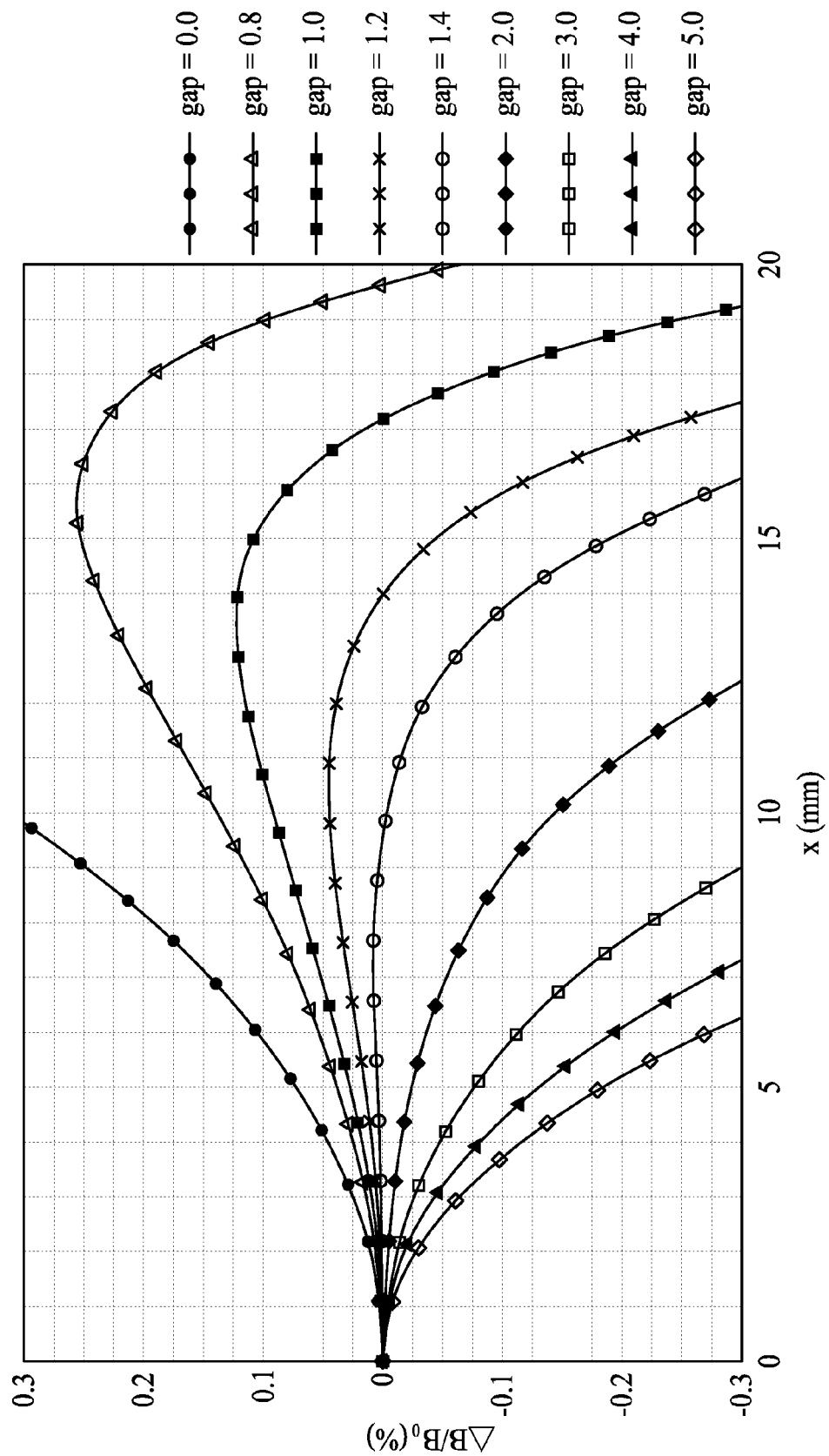
FIG. 5 is a plot showing the variation rate ($\Delta B/B_0$) of the magnetic field generated by the apparatus along the X-axis in accordance with embodiments of the inventive arrangements disclosed herein.

FIG. 5 is a plot showing the variation rate ($\Delta B/B_0$) of the magnetic field generated by the apparatus 10 along the X-axis in accordance with embodiments of the inventive arrangements disclosed herein. In the exemplary embodiments used in FIG. 5, the size of the gap 32 changes from 0.0 mm to 5.0 mm, and the distance between the first segment 31 and the second segment 33 is 51.2 cm. As shown in FIG. 5, the variation rate ($\Delta B/B_0$) of the magnetic field increases for the design without the gap (gap=0.0) in the electrical conductor 30, while the variation rate ($\Delta B/B_0$) of the magnetic field increases near the center and then decreases as the distance to the center increases for the design with the gap that is smaller than 1.2 mm in the electrical conductor 30. In particular, the variation rate ($\Delta B/B_0$) of the magnetic field decreases as the distance to the center increases for the design with the gap that is larger than 1.2 mm in the electrical conductor 30.

Figure 6:
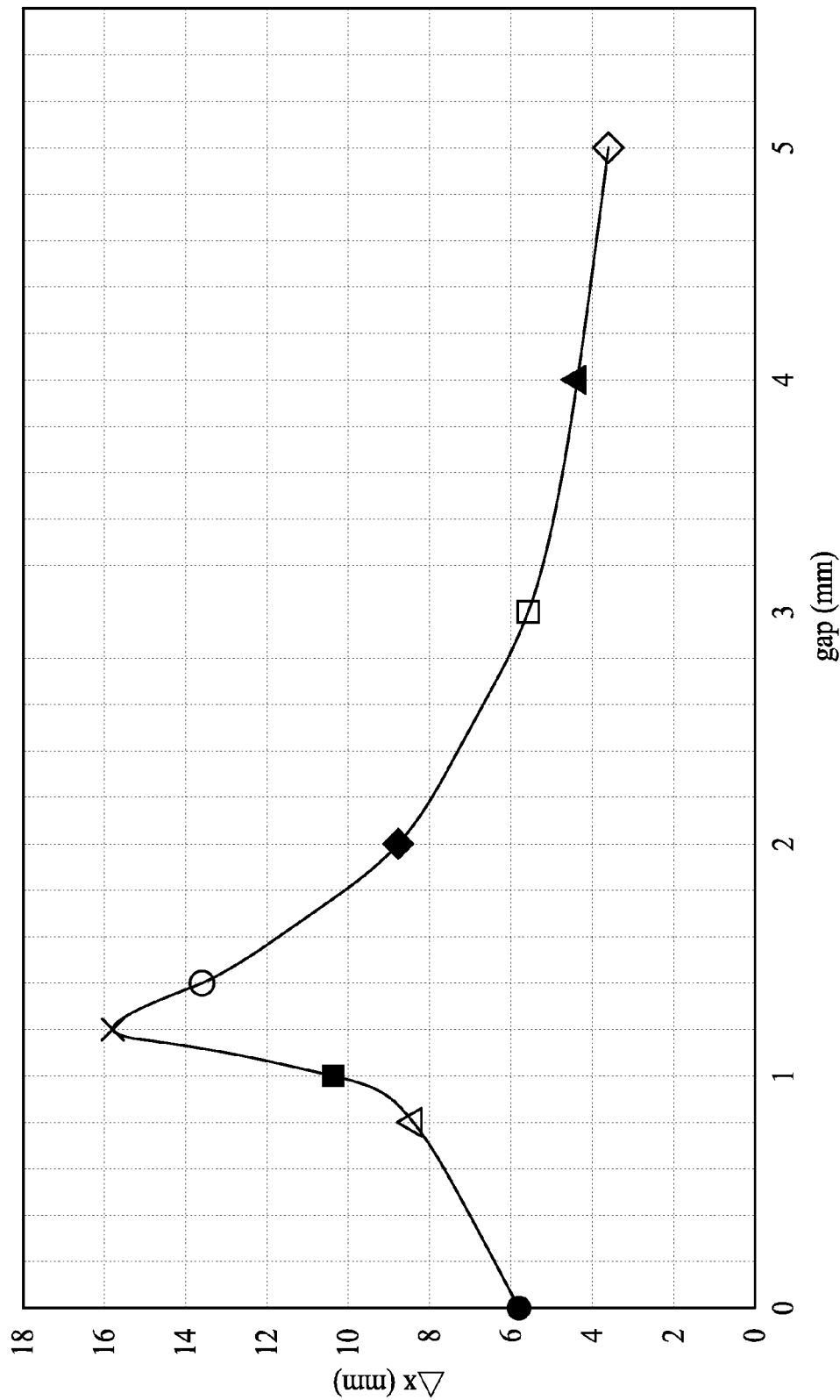
FIG. 6 is a plot showing the relation between a width ($\Delta x$) of a utilizable field region with respect to the size of the gap in accordance with embodiments of the inventive arrangements disclosed herein.

FIG. 6 is a plot showing the relation between a width ($\Delta x$) of a utilizable field region with respect to the size of the gap in accordance with embodiments of the inventive arrangements disclosed herein. In the exemplary embodiments used in FIG. 6, the size of the gap 32 changes from 0.0 mm to 5.0 mm, and the distance between the first segment 31 and the second segment 33 is 51.2 cm. In some embodiment of the present disclosure, the utilizable field region is defined as, but not limited to, the region of the chamber having a variation rate ($\Delta B/B_0$) of a magnetic field that is smaller than a certain value (for example, 0.1). In view of this exemplary definition, FIG. 6 can be plotted in view of FIG. 5. As shown in FIG. 6, the width ($\Delta x$) of the utilizable field region can be increased up to 16.0 mm by fixing the distance between the first segment 31 and the second segment 33 of the electrical conductor 30. In other words, by introducing the gap 32 in the electrical conductor 30, the width ($\Delta x$) of the utilizable field region is can be increased without increasing the distance between the first segment 31 and the second segment 33, i.e., without increasing the size of the entire apparatus 10.

Figure 7:
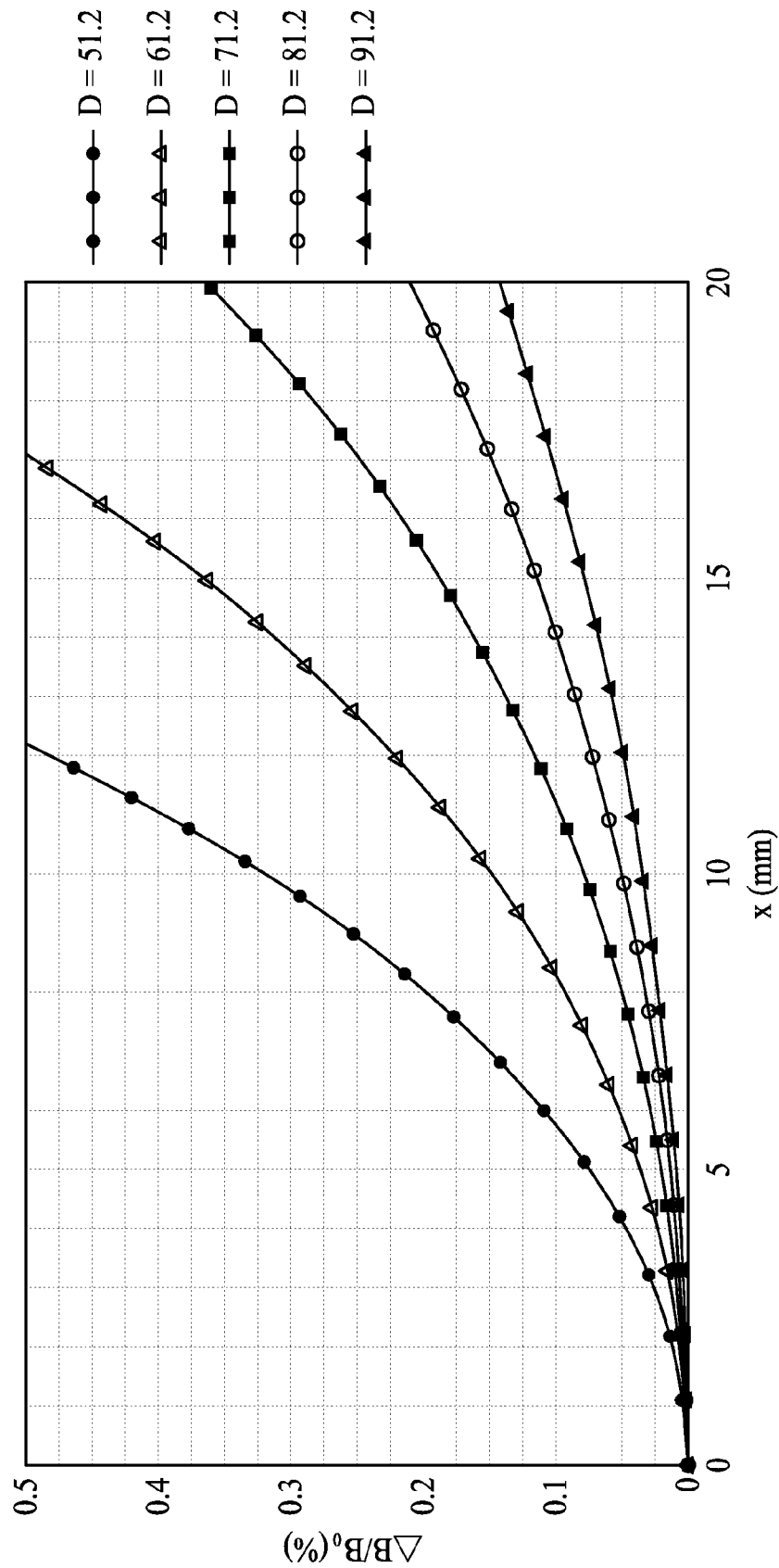
FIG. 7 is a comparison plot showing the variation rate ($\Delta B/B_0$) of the magnetic field generated by comparative apparatuses having the electrical conductor without the gap.

FIG. 7 is a comparison plot showing the variation rate ($\Delta B/B_0$) of the magnetic field generated by comparative apparatuses having the electrical conductor without the gap. In the comparative apparatuses, the distance (D) between the first segment and the second segment of the electrical conductor without the gap is 51.2 cm, 61.2 cm, 71.2 cm, 81.2 cm, and 91.2 cm. As shown in FIG. 7, the variation rate ($\Delta B/B_0$) of the magnetic field increases as the distance to the center increases; in addition, the variation rate ($\Delta B/B_0$) of the magnetic field decreases as the distance (D) between the first segment and the second segment increases.

Figure 8:
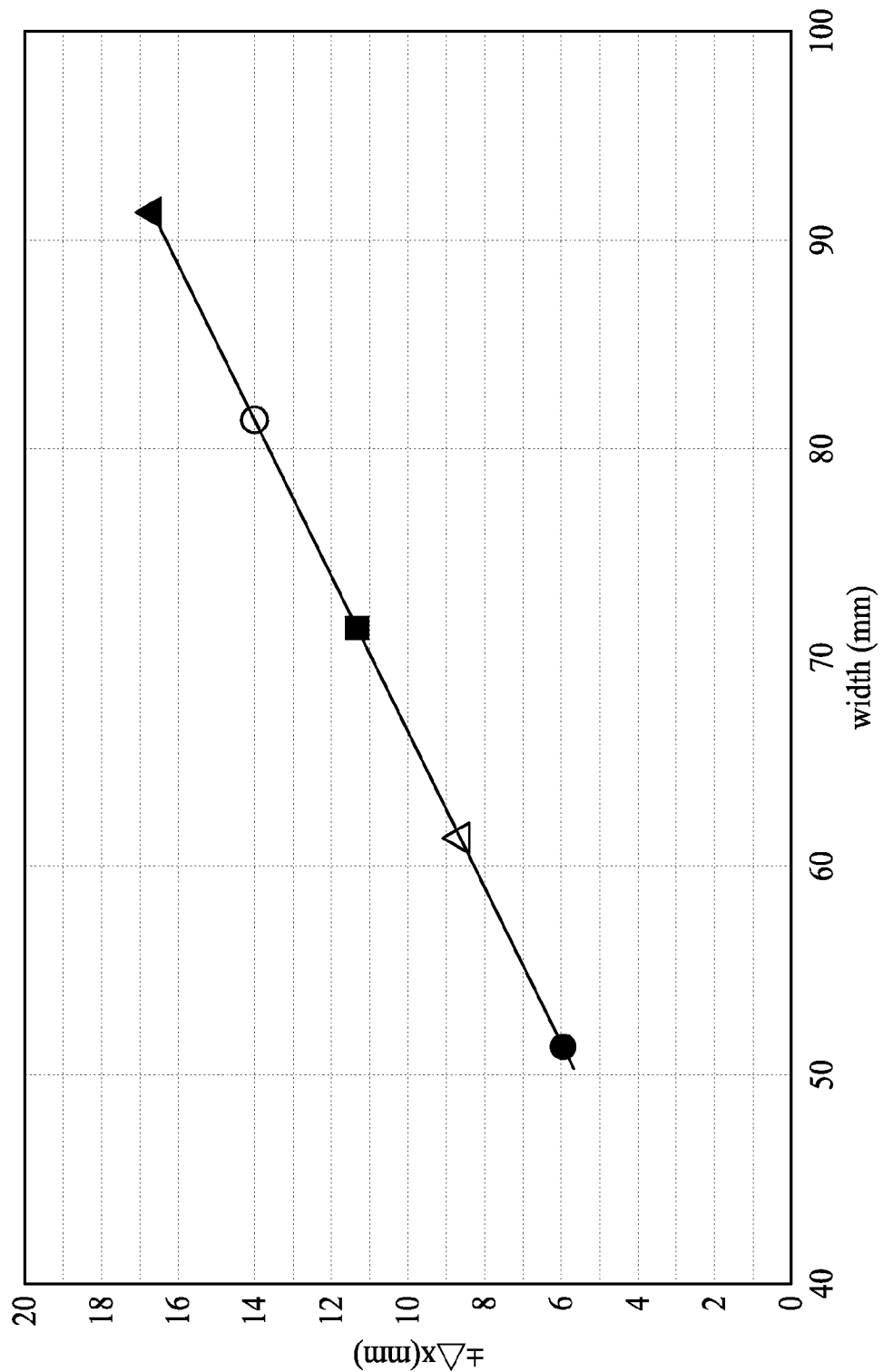
FIG. 8 is a plot showing the relation between a width ($\Delta x$) of a utilizable field region with respect to the distance (D) between the first segment and the second segment.

FIG. 8 is a plot showing the relation between a width ($\Delta x$) of a utilizable field region with respect to the distance (D) between the first segment and the second segment. Based on the same definition for the utilizable field region (the region of the chamber having the variation rate ($\Delta B/B_0$) of the magnetic field that is smaller than a certain value (for example, 0.1)), FIG. 8 can be plotted in view of FIG. 7.

As shown in FIG. 8, the width ($\Delta x$) of the utilizable field region increases as the distance (D) between the first segment and the second segment increases. In other words, without the gap in the electrical conductor, the width ($\Delta x$) of the utilizable field region can be increased by increasing the distance (D) between the first segment and the second segment, i.e., increasing the size of the entire apparatus. In contrast, the embodiment of the present disclosure introduces the gap 32 in the electrical conductor 30, and the width ($\Delta x$) of the utilizable field region can be increased without increasing the distance between the first segment 31 and the second segment 33, i.e., without increasing the size of the entire apparatus 10.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. An apparatus for generating a pulsed magnetic field, comprising:
    an insulating body;
    an electrical conductor positioned on the insulating body; and
    a ferromagnetic body having a hollow portion, wherein the insulating body and the electrical conductor are positioned in the hollow portion;
    wherein the electrical conductor has at least one gap separating the electrical conductor into at least two parts, thereby allowing a current to flow through the at least two parts in parallel to generate a magnetic field in the insulating body,
    wherein the electrical conductor comprises:
        a first segment positioned on the insulating body; and
        a second segment positioned on the insulating body, wherein the first segment is opposite to the second segment, and
    wherein the first segment is a plate, and the at least one gap separates the first segment into a first upper part and a first lower part.

2. The apparatus for generating a pulsed magnetic field of claim 1, wherein the first segment and the second segment are configured to conduct the current in series.

3. The apparatus for generating a pulsed magnetic field of claim 1, wherein the first segment is positioned on a first wall of the insulating body, the second segment is positioned on a second wall of the insulating body, and the second wall is opposite to the first wall.

4. The apparatus for generating a pulsed magnetic field of claim 1, wherein the second segment is a plate, and the at least one gap separates the second segment into a second upper part and a second lower part.

5. The apparatus for generating a pulsed magnetic field of claim 4, further comprising a third segment connecting the first segment and the second segment.

6. The apparatus for generating a pulsed magnetic field of claim 5, wherein the third segment connects the first upper part to the second lower part.

7. The apparatus for generating a pulsed magnetic field of claim 5, wherein the third segment connects the first lower part to the second upper part.

8. The apparatus for generating a pulsed magnetic field of claim 4, further comprising an input terminal connecting the first upper part and the first lower part.

9. The apparatus for generating a pulsed magnetic field of claim 4, further comprising an output terminal connecting the second upper part and the second lower part.

10. The apparatus for generating a pulsed magnetic field of claim 1, wherein the insulating body is a tube.

11. The apparatus for generating a pulsed magnetic field of claim 1, wherein the insulating body comprises ceramic material.

12. An apparatus for generating a pulsed magnetic field, comprising:
    an insulating body;
    an electrical conductor positioned on the insulating body; and
    a ferromagnetic body having a hollow portion, wherein the insulating body and the electrical conductor are positioned in the hollow portion;
    wherein the electrical conductor has at least one gap separating the electrical conductor into at least two parts, thereby allowing a current to flow through the at least two parts in parallel to generate a magnetic field in the insulating body, and
    wherein the electrical conductor forms a one-turn coil on the insulating body without circumferentially surrounding the insulating body.

* * * * *